US 6,702,737 B2

(12) United States Patent
Hino et al.

(10) Patent No.: US 6,702,737 B2
(45) Date of Patent: Mar. 9, 2004

(54) BENDING MANIPULATION DEVICE FOR ENDOSCOPE

(75) Inventors: Kazuhiko Hino, Saitama (JP); Haruo Akiba, Ibaraki (JP); Hiroyuki Arai, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/108,983

(22) Filed: Mar. 29, 2002

(65) Prior Publication Data

US 2002/0143238 A1 Oct. 3, 2002

(30) Foreign Application Priority Data

Mar. 30, 2001 (JP) .......................... 2001-100885
Mar. 30, 2001 (JP) .......................... 2001-101064

(51) Int. Cl.⁷ .............................................. A61B 1/005
(52) U.S. Cl. ....................................... 600/146; 600/149
(58) Field of Search ................................ 600/146, 147, 600/148, 149, 150, 434, 435, 585; 604/95.01, 95.04

(56) References Cited

U.S. PATENT DOCUMENTS

| 4,273,111 A | * | 6/1981 | Tsukaya ..................... 600/145 |
| 4,996,974 A | * | 3/1991 | Ciarlei ........................ 600/149 |
| 5,167,221 A | * | 12/1992 | Chikama ..................... 600/149 |
| 5,328,467 A | * | 7/1994 | Edwards et al. ......... 604/95.01 |
| 5,395,327 A | * | 3/1995 | Lundquist et al. .......... 604/528 |
| 6,033,378 A | * | 3/2000 | Lundquist et al. ....... 604/95.01 |
| 2001/0034472 A1 | * | 10/2001 | Fujii et al. .................. 600/146 |

FOREIGN PATENT DOCUMENTS

JP          08-082749          3/1996

* cited by examiner

Primary Examiner—John P. Leubecker
(74) Attorney, Agent, or Firm—Rabin & Berdo, P.C.

(57) ABSTRACT

A bending manipulation device for endoscope wherein a pair of control wires are taken up by a pulley provided in and given a rotary motion by the main control portion of the endoscope, and one of control wires extended out from the pulley corresponding to the turning operation thereof is taken up by the pulley while the other is paid out from the pulley, thereby enabling the bending manipulation to be carried out. The groove of the above pulley is formed in the shape of a spiral continuously extending in the peripheral direction of this pulley and is used in common by the above pair of control wires. One part from the one end of the groove and the other part from the other end of the groove are arranged side by side and in parallel with each other. Each of control wires is alternately taken up on the groove of the pulley corresponding to the turning direction of the pulley.

8 Claims, 15 Drawing Sheets

(a)  (b)  (c)

(a)

(b)

(c)

BENDING MANIPULATION DEVICE FOR ENDOSCOPE

FIELD OF THE INVENTION

The present invention relates to an endoscope, and more particularly to a bending manipulation device for the endoscope, which is capable of directing the bending portion in the insertion part of the endoscope to the desired direction by turning an angle knob provided in the main control portion of the endoscope.

BACKGROUND OF THE INVENTION

In general, the endoscope is made up of the main control portion and a flexible insertion portion which is connected with the above operation portion and inserted into an objective body, for instance, a human body and other things, which need observation, inspection, and so forth of their inside. This insertion portion is made up of a flexible soft portion connected with the operation portion, a flexible bending portion connected with the tip side of the above flexible soft portion, and a hard tip distal end portion connected with the tip of the above bending portion and provided with a objective window (lens) or the like necessary for observation, inspection, etc. of the inside of the objective body.

In order to manipulate the above bending portion, the endoscope includes a bending manipulation device in the above main control portion. With regard to the bending manipulation device of this kind, the Japanese patent publication No. 8-82749 has already disclosed that which has such a structure as shown in FIG. 15 of the accompanying drawings attached to this specification. Referring to this figure, a pulley 10 is rotated by means of the angle knob provided in the main control portion of the endoscope. The pulley 10 includes two parallel groves independently prepared for every control wire. Control wires 12, 14 are taken up by two grooves, respectively. The bending manipulation device is constituted such that as the pulley 10 is rotated, one of control wires 12, 14 extending out from the pulley 10 is taken up by the pulley 10 corresponding to the rotation of the pulley 10 while the other is paid out from the pulley 10, thereby enabling the bending manipulation of the bending portion to be carried out.

In order to improve the observation performance of the endoscope, it is desirable to increase or widen the range of the angle that the above-mentioned bending portion is allowed to be curved. In order to achieve this, it is required to increase the wire stroke of the control wire.

There have been proposed certain constitutions for increasing the above wire stroke. One of them, for instance, is to increase the winding diameter of the pulley 10 by which control wires 12, 13 are taken up. However, an increase in the winding diameter of the pulley 10 results in an increase in the rotational torque of the pulley 10, which causes such a problem that the angle knob (referred to simply as 'angle knob' hereinafter) comes to require a larger force for turning it.

There have been also proposed certain constitutions for decreasing the rotational torque of the pulley 10. One of them, for instance, is to decrease the winding diameter of the pulley 10. However, in the constitution like this, the smaller the winding diameter of the pulley 10 is made, the more the angle knob has to be turned more until the bending portion takes the same angle, so that difficulty in handling the endoscope remains. Furthermore, if trying to make the wire stroke still larger, control wires 12, 14 have to be wound more than one turn on the same groove of the pulley 10 as shown in FIG. 15. As a result of that, the winding diameter gradually becomes larger, the torque becomes larger, and operation with constant torque becomes impossible. At the same time, the overlapped control wires come to interfere with each other and rub together, which reduces the durability of control wires.

There have been further proposed certain constitutions for avoiding that one control wire is taken up more than one turn on the same groove of the pulley 10, in other words, a so-called double winding of the control wire onto a single groove. It is one of them, for instance, to form two spiral grooves extending in the axial direction of the pulley 10, each groove being separately used by each of two control wires. According to this constitution, however, the pulley 10 is required to have a width allowing at least a two step groove portions for one control wire to be provided in the axial direction of the pulley 10. As two control wires are used in order to curve the curve portion in the up/down directions, the pulley 10 has to have a width allowing four step groove portions in total. Furthermore, as two control wires have to be added in order to curve the bending portion in the right/left directions, the pulley 10 has to have a width allowing eight step groove portion to be prepared therein. Thus, if adopting a constitution like the above, the pulley 10 must have a larger space in the axial direction thereof, by which the whole weight of the endoscope is increased. Therefore handling the endoscope is more difficult.

The invention has been made in view of such problems as described above, and the principal object of the invention is to provide a novel and improved bending manipulation device for the endoscope, which is capable of preventing the rotational torque from becoming larger at the time of executing the bending manipulation, avoiding interference between control wires, facilitating the miniaturization of the device, and making the stroke of the control wire much larger.

SUMMARY OF THE INVENTION

According to the invention, in order to solve problems as described above, there is provided a bending manipulation device for an endoscope which include a pulley provided in and given a rotary motion by the main control portion of the endoscope; at least a pair of control wires, each of which winds one end portion thereof on to the pulley and extends out the other end portion thereof from the pulley such that one of the extended control wires is taken up by the pulley while the other of the same is paid out from the pulley corresponding to the rotation of the pulley, thereby enabling the bending manipulation over the bending portion to be carried out; and at least one common groove formed on the periphery of the pulley to continuously extend in the peripheral direction of the pulley, and commonly used by the pair of control wires for winding themselves thereon.

According to the constitution of the bending manipulation device as described above, various advantageous effects can be obtained as follows. That is, the groove of the pulley for taking up a pair of control wires is formed as a single groove continuously extending in the peripheral direction of the pulley, so that the double winding of each control wire can be avoided. Because of this, it becomes possible to prevent the increase in the rotational torque caused at the time of executing the bending manipulation, and also, to avoid the interference between the same control wires.

Furthermore, each of control wires is alternately taken up on the groove of the pulley corresponding to the turning direction of the pulley. As one of control wires is taken up on the groove, this control wire gradually uses the groove of the pulley. At this time, the other control wire is paid out from the pulley, so that the groove of the pulley comes into the unused state gradually. Consequently, as there is neither the chance that the groove of the pulley is used by two control wires at a time, nor the chance that the control wires interferes with each other.

Still further, as the groove of the pulley is formed as a single groove continuously extending in the peripheral direction of the pulley, each control wire is able to commonly use this groove, so that it becomes possible to make the length of the groove shorter than that used in the prior art case wherein the groove has been provided for each of the control wires. At the same time, it becomes also possible to reduce the number of steps of the groove, whereby the space in the axial direction of the pulley is saved and the miniaturization of the device is facilitated.

Still further, in the bending manipulation device according to the invention, the groove is constituted such that one part from the one end of the groove and the other part from the other end of the same are formed in parallel with each other while each of the control wires is alternately taken up on the groove, so that the stroke of each control wire can be made longer.

BRIEF DESCRIPTION OF THE DRAWINGS

The above and other features of the invention and the concomitant advantages will be better understood and appreciated by persons skilled in the field to which the invention pertains in view of the following description given in conjunction with the accompanying drawings which illustrate preferred embodiments.

In the accompanying drawings.

DETAILED DESCRIPTION OF THE PREFERRED EMBODIMENTS

The invention will now be described in detail by way of certain examples of a bending manipulation device of the endoscope according to the preferred embodiments of the invention, with reference to the accompanying drawings.

Figure 1:
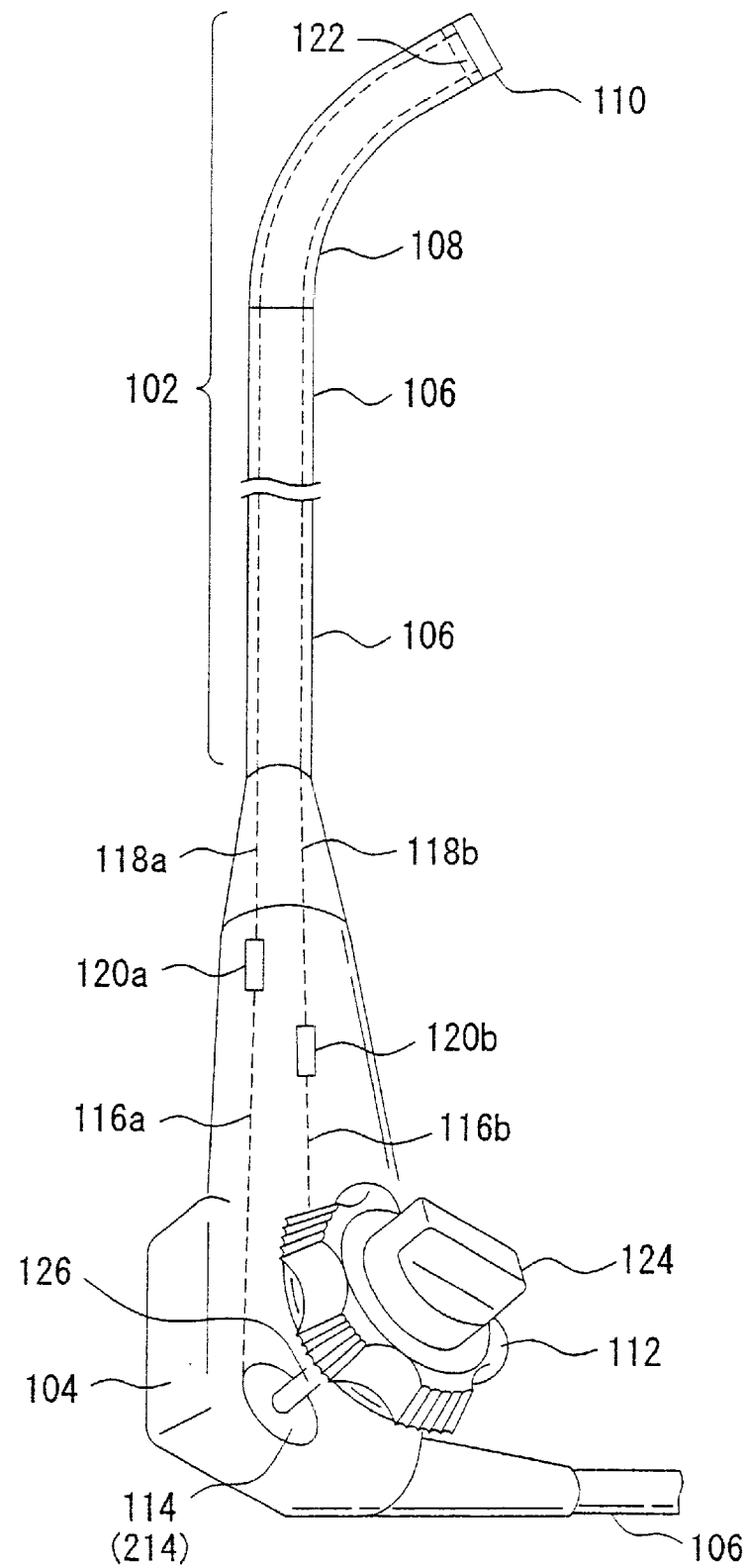
FIG. 1 is a schematic illustration for giving an outline of the constitution of an endoscope to which the invention is applicable.

First of all, let us start from description about the entire structure of the endoscope, to which the invention is applicable, with reference to the accompanying drawings. FIG. 1 is a schematic illustration for giving an outline of the constitution of the endoscope as used for the medical care or the like. In general, the structure of the endoscope can be roughly divided into the following portions, that is, an insertion portion 102 directly inserted into the somatic cavity; a main control portion 104 provided at and connected with the base end portion of the insertion portion 102; and a universal electrical cord portion 105 drawn out from the main control portion 104 and connected with a light source and a processor as well.

The above insertion portion 102 is mainly made up of a flexible soft portion 106 connected with the main control portion 104; a bending portion 108 flexibly formed and connected with the flexible soft portion 106 on the tip end side thereof; a hard tip distal end portion 110 connected with the tip end of the bending portion 108 and provided with an observation objective window (lens), a light objective window (lens), outlets for air/water supply, a forceps channel, and so forth.

This endoscope is provided with a bending manipulation device capable of curving the above bending portion 108 in at least two directions (up and down directions, for instance) at a predetermined angle. This bending manipulation device is constituted as follows, for instance. An angle knob 112 performing the bending manipulation over the curve of the bending portion 108 is rotatively fitted to the casing of the main control portion 104. Inside the main control portion 104, there is rotatively provided a pulley 114 which is driven by the angle knob 112. According to the present embodiment, each control wire comprises a manipulating wire 116a (116b) and a connection wire 118a (118b) which are connected with each other by a connection member 120a (120b). Accordingly the manipulating wires 116a, 116b are parts of the control wires. Each end portion of a pair of manipulating wires 116a and 116b is taken up on the groove of the pulley 114. The other end portion of these manipulating wires 116a, 116b is extended out from the pulley 114 in the tangential direction of the pulley 114. The constitution of the pulley 114 will be described in detail later.

The other end portions of manipulating wires 116a, 116b extended out from the above pulley 114 are respectively connected with square rod-shaped connection members 120a, 120b for connecting the above manipulating wires 116a, 116b with connection wires 118a, 118b. These connection members 120a, 120b are supported inside the operation portion 104 such that they are allowed to do the reciprocating motion along a guide (not shown). Connection wires 118a, 118b are fixed to a sleeve 122 provided inside the tip end portion of the bending portion 108. These manipulating wires 116a, 116b and connection wires 118a, 118b are stranded wires formed by stranding a lot of fine stainless steel wires, for instance. These manipulating wires 116a, 116b and connection wires 118a, 118b may be coated with synthetic resin or covered with a pertinent material in order to enhance the durability thereof. Still further, the operation portion 102 may be provided with a locking knob 124 as shown in FIG. 1, for temporally locking the angle knob 112 to fix the angle of the bending portion 108 for a certain period of time.

As described above, in the bending manipulation device, if the pulley 114 is rotated by turning the angle knob 112, one of manipulating wires 116a, 116b extended out from the pulley 114 is taken up by the pulley while the other is paid out from the pulley corresponding to the rotation of the pulley 114, whereby the bending portion 108 is curved and kept at a predetermined angle.

First Embodiment

Figure 2:
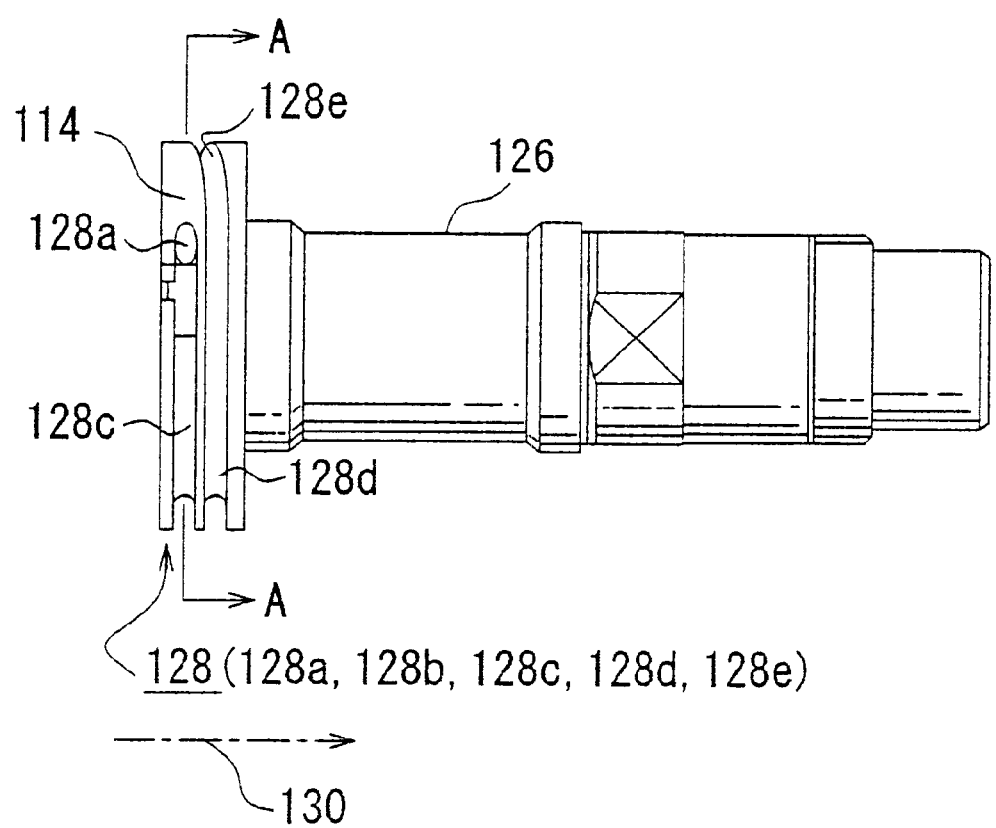
FIG. 2 is a diagram showing the constitution of the outside appearance of a pulley of the endoscope according to the first embodiment of the invention.

In the next, the constitution of the pulley 114 according to the first embodiment of the invention will be described with reference to FIGS. 2 through 8. FIG. 2 is a diagram showing an exterior view of the pulley 114, FIG. 3 is a sectional side view of the pulley 114, FIG. 4 is a sectional view of the pulley 114, taken along the A—A line of FIG. 2, and FIG. 5 is an expanded plan view showing the groove 128 of the pulley 114 in the state shown in FIG. 4.

Figure 3:
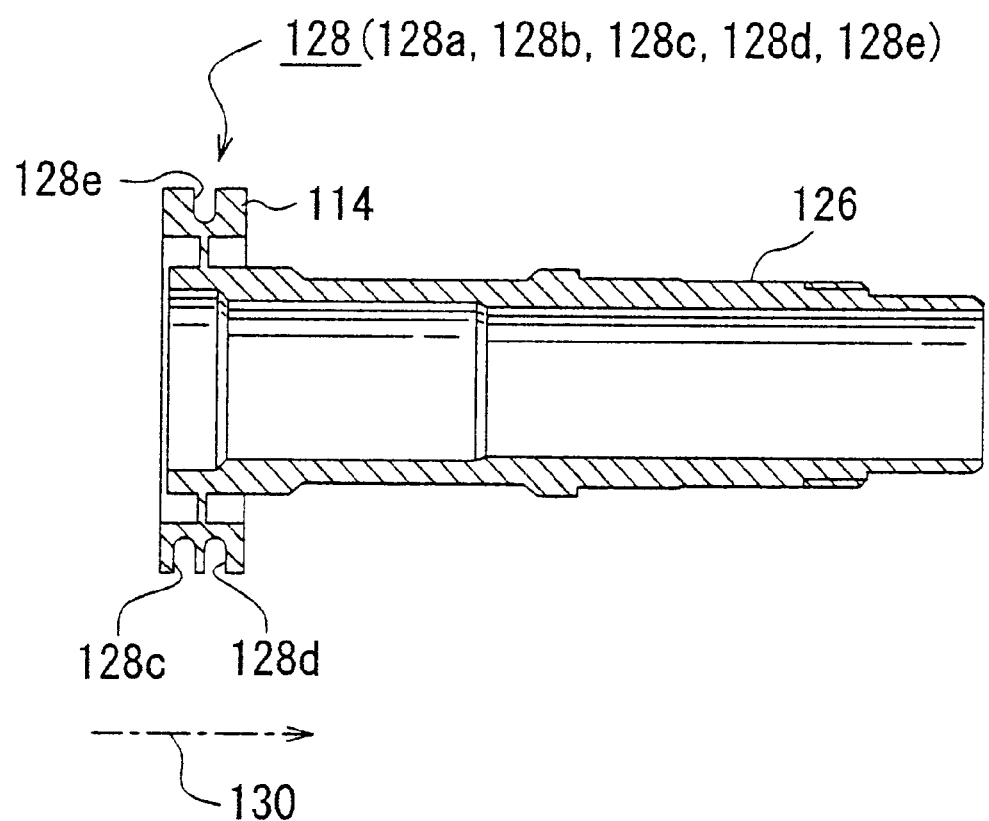
FIG. 3 is a sectional side view showing the constitution of a pulley of the endoscope according to the first embodiment of the invention.

As will be seen from FIGS. 2 and 3, the above pulley 114 is fitted to one end portion of the pulley axle 126. This pulley axle 126 is formed in the shape of an almost circular tube and the other end portion thereof is fitted to the angle knob 112 as shown in FIG. 1. To put it more concretely, the angle knob 112 has a fitting hole (not shown) as formed on its inside peripheral surface, and the pulley axle 126 is fitted to the angle knob 112 through this fitting hole. Thus, the rotation of the angle knob 112 is transmitted to the pulley axle 126 to rotate it, thereby the pulley 114 being rotated by an angle corresponding to the turning angle of the angle knob 112.

Figure 4:
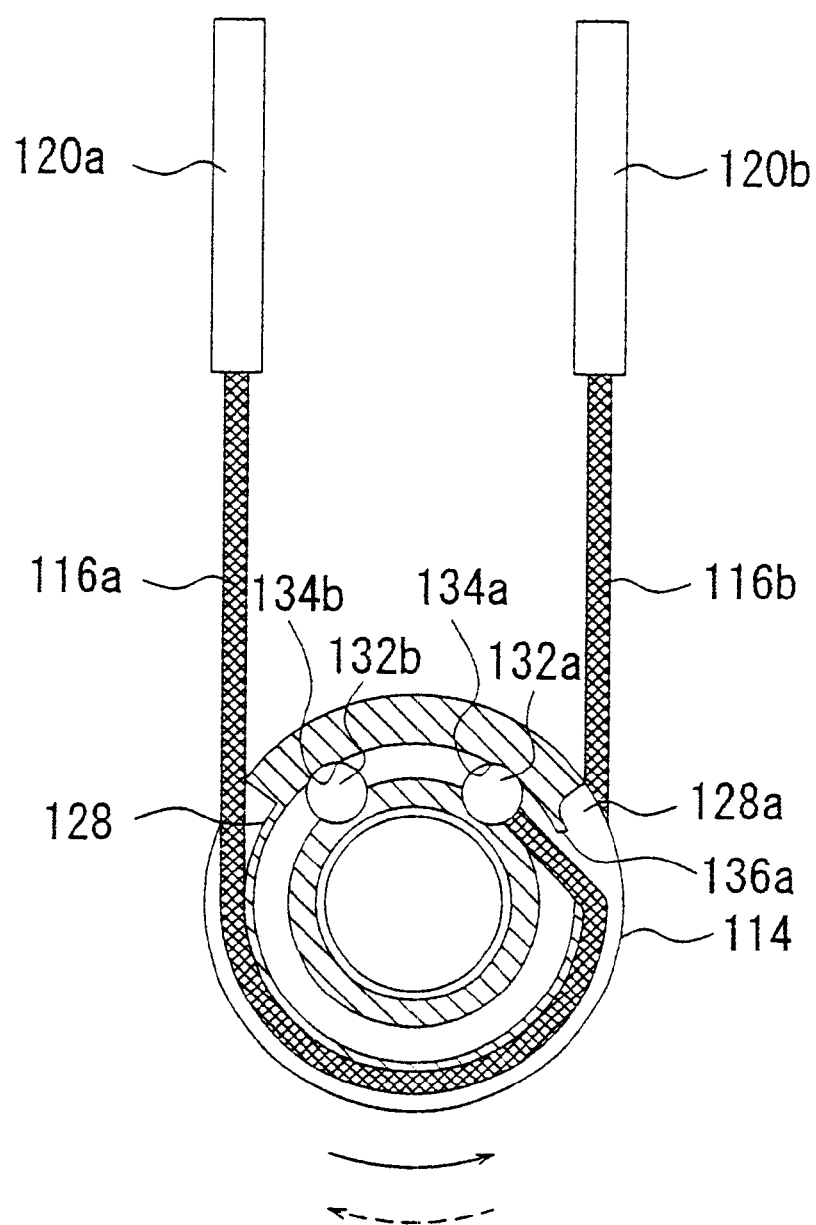
FIG. 4 is a sectional view taken along the A—A line of FIG. 2 for showing the constitution of a pulley of the endoscope according to the first embodiment of the invention.
Figure 5:
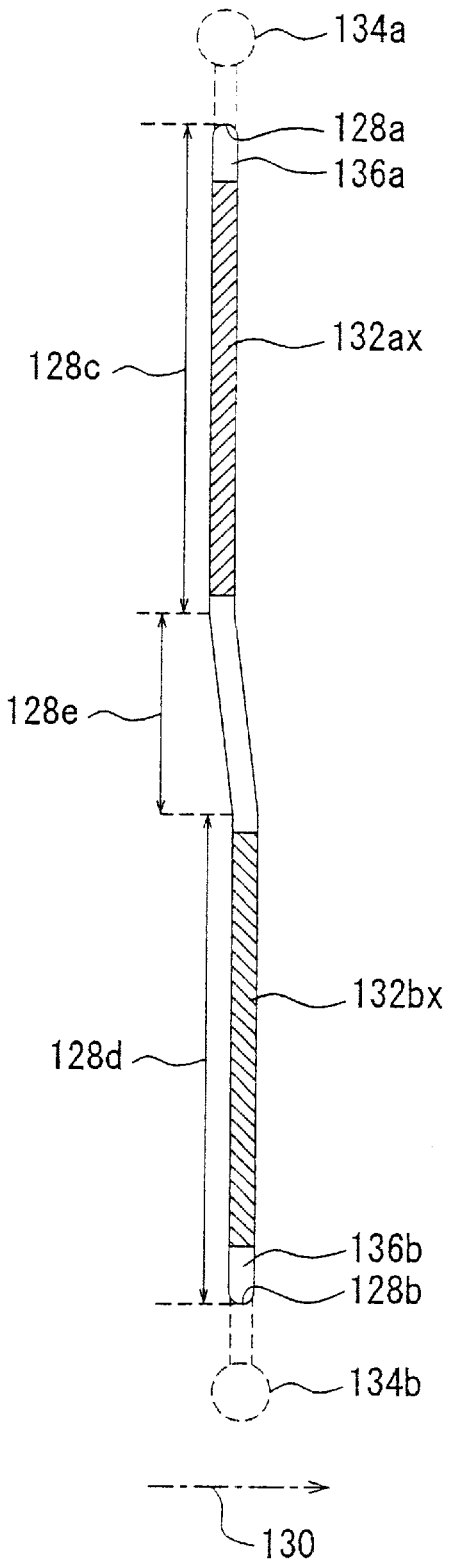
FIG. 5 is an expanded view obtained by expanding, on a plane, only the groove formed along the periphery of the pulley of the endoscope according to the first embodiment of the invention.

Referring to FIG. 4, the above pulley 114 has a groove 128 as formed on the external periphery thereof, and manipulating wires 116a, 116b are taken up on the groove 128. As will be seen from FIGS. 2 through 5, this groove 128 is formed in the shape of a spiral continuously extending in the peripheral direction of the above pulley 114. The groove 128 is made up of a groove portion (first step groove portion) 128c beginning from one end 128a of the groove 128, another groove portion (second step groove portion) 128d beginning from the other end 128b of the groove 128, and another groove portion (shift step groove portion) 128e connecting both of the first and second groove portions 128c and 128d with each other.

To put it more in detail, as shown in FIG. 2, the first step groove portion 128c is formed on the first plane obtained by cutting the pulley 114 in the direction perpendicular to the axis of the pulley 114. The second step groove portion 128d is formed in parallel with the above first step groove portion 128c on the second plane obtained by shifting the above first plane almost in parallel with the axial direction of the pulley 114 as indicated by an arrow 130 (single dot chain line). As a result of this, the first and second step groove portions 128c, 128d are arranged side by side in parallel with each other. In addition, the shift step groove portion 128e having these first and second step groove portions 128c, 128d communicating with each other is formed such that it is gradually shifted from the first plane to the second one in the axial direction 130 of the pulley 114.

That is, if only the groove 128 is expanded on a plane, it is drawn in such a shape as indicated in FIG. 5. As will be seen from this figure, the first and second step groove portions 128c and 128d become almost linear although they are shifted a little in the axial direction 130 of the pulley 114 due to a gentle slope located therebetween. On the one hand, the shift step groove portion 128e having both of groove portions 128c and 128d communicating with each other is formed to become a slant line slanting in the axial direction 130 of the pulley 114.

As shown in FIG. 4, in the vicinity of one end 128a of the groove 128 in the above pulley 114, there are formed circular tube-like coupling holes 134a, 134b capable of receiving spherical coupling members 132a, 132b from the side of the pulley 114, respectively. These spherical coupling members 132a, 132b are fitted to one end of manipulating wires 116a, 116b, respectively. To put it more concretely, as shown in FIGS. 4 and 5, for instance, the coupling hole 134a is provided in a region beyond one end 128a of the groove 128 in the peripheral direction of the pulley 114 as indicated by an arrow (solid line). On the other hand, the coupling hole 134b is provided in a region beyond the other end 128b of the groove 128 in the peripheral direction of the pulley 114 as indicated by an arrow (dotted line). Each center of coupling holes 134a, 134b is positioned so as to externally go away from the pulley axle 126 in the radial direction of the pulley 114 and positioned on the center side of the groove 128 rather than the bottom of the groove 128.

As shown in FIGS. 4 and 5, in one end 128a of the groove 128, there is provided a communication hole 136a communicating with the above coupling hole 134a while in the other end 128b of the groove 128, there is provided a communication hole 136b communicating with the above coupling hole 134b. The above communication hole 136a opens to one side surface (left side surface in the figure) of the pulley 114 as shown in FIG. 2 while the above communication hole 136b opens to the other side surface (right side surface in the figure) of the pulley 114 as shown in FIG. 2.

As shown in FIG. 4, the above manipulating wire 116a inserts the coupling member 132a into the coupling hole 134a of the pulley 114 from one side surface of the pulley 114 and at the same time, passes itself through the communication hole 136a, and then winds itself along the groove 128 of the pulley 114 to set itself on the groove 128. With this, the above manipulating wire 116a is held in the groove 128 of the pulley 114 to be workable in the take-up direction as well as in the pay-out direction. In this way, the manipulating wire 116a is taken up along the groove 128 as the pulley 114 is rotated in the direction as indicated by a solid line arrow (one direction) while it is paid out along the groove 128 as the pulley 114 is rotated in the direction indicated by a dotted line arrow (reverse direction). The manipulating wire 116a in the state shown in FIG. 4 exists in the hatched portion 132ax as shown in FIG. 5.

In contrast, the above manipulating wire 116b inserts the coupling member 132b into the coupling hole 134b of the pulley 114 from the other side surface the pulley 114 and at the same time, passes itself through the communication hole 136b, and then winds itself along the groove 128 of the pulley 114 to set it along the groove 128. With this, the above manipulating wire 116b is held in the groove 128 of the pulley 114 to be workable in the take-up direction as well as the pay-out direction. In this way, the manipulating wire 116b is taken up along the groove 128 as the pulley 114 is rotated in the direction indicated by the dotted line arrow (reverse direction) while it is paid out along the groove 128 as the pulley 114 is rotated in the direction indicated by the solid line arrow (one direction). The manipulating wire 116b in the state shown in FIG. 4 exists in the hatched portion 132bx as shown in FIG. 5.

In the bending manipulation device as constituted like the above according to the first preferred embodiment, the pulley 114 can be rotated in either one of two directions by means of the angle knob 112, whereby one manipulating wire 116a (or 116b) is taken up by the pulley 114 while the other manipulating wire 116b (or 116a) is paid out from the pulley 114, so that the bending portion 108 as shown in FIG. 1 is curved by a desired angle.

The operation of this time will be described in the following, with reference to FIGS. 6(a)–6(c) and 7(a)–7(c). FIGS. 6(a) through 6(c) show the relation between the turning direction of the pulley 114 and the states of manipulating wires 116a, 116b taken up by and paid out from the pulley 114. FIGS. 7(a) through 7(c) are expanded views of the groove 128 obtained by expanding only the groove 128 when manipulating wires 116a, 116b are in respective positions as shown in FIGS. 6(a) through 6(c). In the state shown in FIG. 6(b), both of manipulating wires 116a, 116b extend out from the pulley 114 by the same length, so that the bending portion 108 is in the state where it is not yet curved at any angle.

If the angle knob 112 is operated at first in the state shown in FIG. 6(b) and the pulley 114 is rotated in an arrow direction (dotted line), the other manipulating wire 116b is taken up on the pulley 114 as shown FIG. 6(c) and at the same time, one manipulating wire 116a is paid out from the pulley 114. With this operation, the bending portion 108 is curved in the up (or down) direction, for instance.

At this time, the groove 128 of the pulley 114 is moved from the state of FIG. 7(b) to the state of FIG. 7(c). In other words, as the other manipulating wire 116b is taken up by the pulley 114, the length of the groove 128 of the pulley 114 as used by this manipulating wire 116b gradually becomes longer, and in the state of FIG. 6(c), the manipulating wire 116b makes use of the hatched portion 132bx as shown in FIG. 7(c). In contrast, one manipulating wire 116a is gradually paid out, so that the part of the groove 128 of the pulley 114 used by this manipulating wire 116a gradually becomes smaller, and in the state of FIG. 6(c), the portion of the groove 128 the manipulating wire 116a makes use of is the hatched portion 132ax as shown in FIG. 7(c).

In the next, if the angle knob 112 is operated in the state shown in FIG. 6(b) and the pulley 114 is rotated in the direction as indicated by an arrow (solid line), one manipulating wire 116a is taken up by the pulley 114 as shown FIG. 6(a), and at the same time, the other manipulating wire 116b is paid out from the pulley 114. With this, the bending portion 108 is curved in the down (or up) direction, for instance.

At this time, the groove 128 of the pulley 114 is moved from the state of FIG. 7(b) to the state of FIG. 7(a). In other words, as one manipulating wire 116a is taken up, the length of the groove 128 of the pulley 114 as used by this one manipulating wire 116a gradually becomes longer, and in the state of FIG. 6(a), the manipulating wire 116a makes use of the hatched portion 132ax as shown in FIG. 7(a). In contrast, the other manipulating wire 116b is gradually paid out, so that the part of the groove 128 of the pulley 114 used by this manipulating wire 116a gradually becomes smaller, and in the state of FIG. 6(a), the portion of the groove 128 the manipulating wire 116b makes use of is the hatched portion 132bx as shown in FIG. 7(a).

As described above, according to the first embodiment, the groove of the pulley 114 for taking up a pair of manipulating wires 116a, 116b thereon is formed as a single groove continuously extending in the peripheral direction of the pulley 114, so that there is no need for each of manipulating wires 116a, 116b to be doubly wound in order to earn or to increase the wire stroke. This makes it possible to prevent the rotational torque from being increased at the time of executing the bending manipulation with regard to the bending portion 108 and also to avoid self interference by the same manipulating wire. With this, there can be provided the bending manipulation device which is easy for handling and is able to enhance durability of the manipulating wire.

Furthermore, each of manipulating wires 116a, 116b is alternately taken up on the groove 128 of the pulley 114. In other words, as the one of manipulating wires is taken up by the pulley 114, it gradually uses the groove 128 of the pulley 114, and the other of manipulating wires is gradually paid out from the groove 128 of the pulley 114, whereby the groove 128 of the pulley 114 gradually comes into the unused state. Therefore, there is neither the chance that the groove 128 of the pulley 114 is used by both of manipulating wires 116a, 116b at one time, nor the chance that these two manipulating wires will interfere with each other.

Still further, as the groove of the pulley is formed in the shape of a spiral continuously extending in the peripheral direction of the pulley, each manipulating wire is extended being shifted from the pulley, so that interference between a pair of manipulating wires can be surely avoided, the interference being caused when paying out the manipulating wire from the pulley.

Still further, as the groove 128 of the pulley 114 is formed as a single groove 128 continuously extending in the peripheral direction of the pulley, each of manipulating wires 116a, 116b can use this groove 128 in common. Consequently, the length of the groove 128 can be shortened comparing with the prior art case wherein the groove is separately prepared for every manipulating wire. Especially, in the case of the first embodiment, the groove 128 of the pulley 114 is formed such that the first step groove portion 128c beginning from the one end 128a of the groove 128 and the second step groove portion 128d beginning from the other end 128b of the groove 128 are arranged side-by-side in parallel with each other in the axial direction of the pulley 114. With this groove structure, there can be obtained in the axial direction of the pulley 114 a good enough width or space to allow two step groove portions to be provided. Accordingly, it becomes possible to save more space in the axial direction of the pulley, as compared with the prior art case wherein the space for four step groove portions is needed, and to facilitate the miniaturization of the device. Regarding the length of the groove 128 of the pulley 114, if it is made, for instance, longer than one peripheral length of the pulley 114 but shorter than twice as long as the peripheral length of the pulley 114, the width occupied by that long groove is good enough for providing two step groove portions.

Still further, according to the first embodiment, the groove 128 of the pulley 114 is formed such that the first step groove portion 128c beginning from the one end 128a of the groove 128 and the second step groove portion 128d beginning from the other end 128b are arranged side by side in parallel with each other in the axial direction of the pulley 114, and is constituted such that each of manipulating wires 116a, 116b is alternately taken up on the groove 128 of the pulley 114 corresponding to the turning direction of the pulley 114. For this, the groove 128 of the pulley 114 can be commonly used by each of manipulating wires 116a, 116b, so that the wire stroke of each of manipulating wires 116a, 116b can be made longer by the amount resulting from the above groove structure.

Still further, according to the first embodiment, one manipulating wire fixedly holds its one end in the vicinity of the one end 128a of the groove 128 while the other manipulating wire fixedly holds its one end in the vicinity of the other end 128b of the groove 128. With this structure, it becomes possible to use a still longer part of the groove 128 for taking up and paying out the manipulating wire. With this, it becomes possible to make the wire stroke of the manipulating wire as long as possible.

Figure 8:
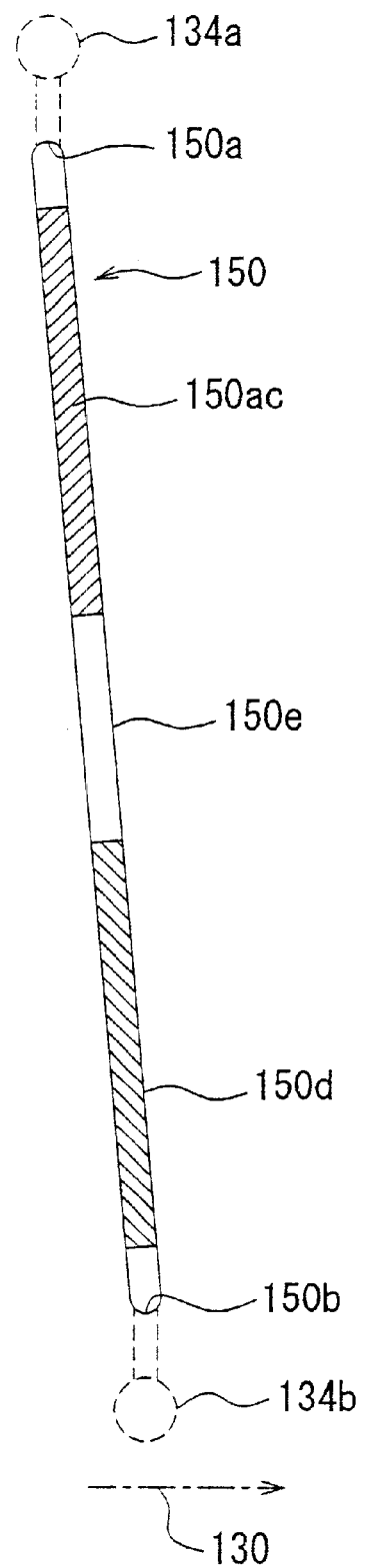
FIG. 8 is an expanded plan view showing another constitution of the groove provided along the periphery of the pulley of the endoscope according to the first embodiment of the invention.

The groove formed on the periphery of the above pulley 114 may be formed in the shape of a spiral continuously extending in the axial direction of the pulley 114. Thus, it may be possible to form such a groove that gradually and continuously slants in the axial direction 130 of the pulley 114 as shown in FIG. 8. If the groove takes the constitution as described above, the expanded view of the groove 150 is drawn as a slanted straight line as shown in FIG. 8 when expanding it on a plane.

Figure 6:
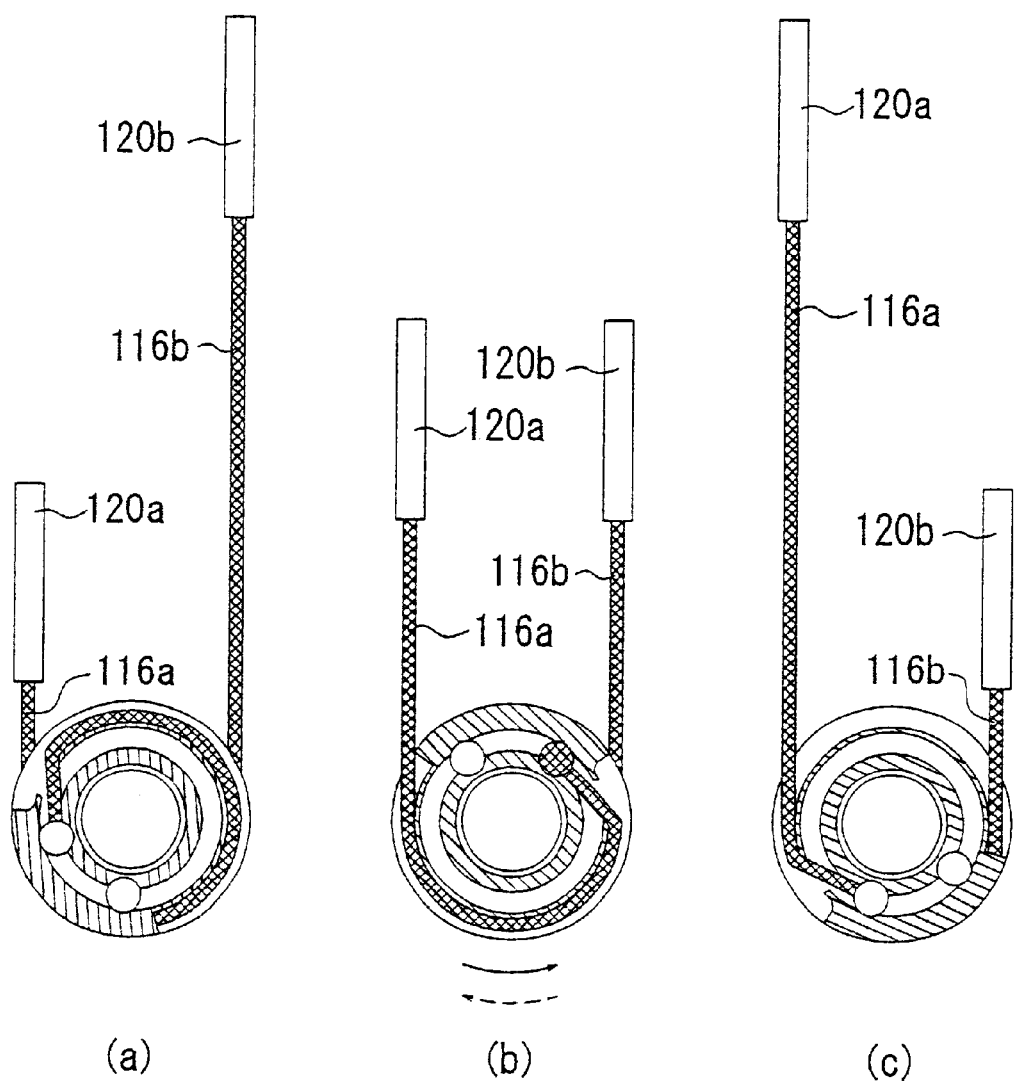
FIGS. 6(a) through 6(c) are illustrations for describing the operation of the pulley of the endoscope according to the first embodiment of the invention.
Figure 7:
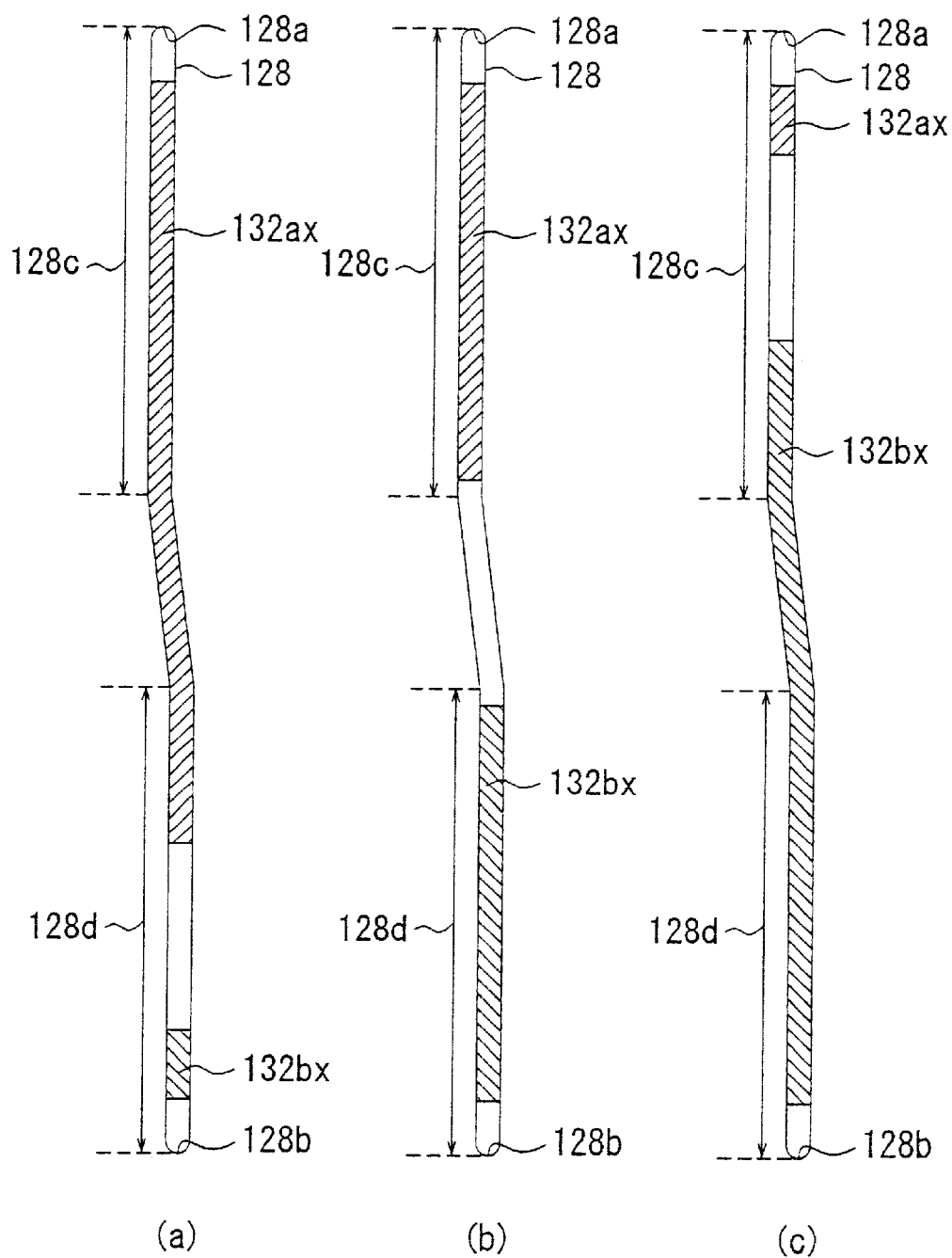
FIGS. 7(a) through 7(c) are illustrations for describing the operation of the pulley of the endoscope according to the first embodiment of the invention.

The groove portion 150a in FIG. 8 corresponds to the groove portion 128a in FIG. 6, the groove portion 150b in FIG. 8 corresponds to the groove portion 128b in FIG. 6, the groove portion 150c in FIG. 8 corresponds to the groove portion 128c in FIG. 6, the groove portion 150d in FIG. 8 corresponds to the groove portion 128d in FIG. 6, and the groove portion 150e in FIG. 8 corresponds to the groove portion 128e in FIG. 6, respectively. Similar to the example as described above, the groove 150 may be formed by shifting it in the axial direction 130 of the pulley 114 such that the expanded view of it shows a straight line.

The first embodiment has been described so far by way of the example wherein the bending manipulation is carried out to direct the bending portion 108 in the upward and downward directions by means of two manipulating wires 116a, 116b. As a matter of course, however, the invention should not be limited by this example. The bending manipulation can be executed to direct the bending portion 108 in the right and left directions by means of the two manipulating wires 116a, 116b.

Furthermore, if there are additionally provided the following items, that is, another angle knob, another pulley rotated independently by the above another angle knob and provided with the same groove as the groove 128 of the existing pulley 114 as previously described, and the same two manipulating wires fitted to another pulley as those fitted to the existing pulley 114, the bending manipulation can be carried out to direct the bending portion 108 in two kinds of directions, that is, the directions of up/down and right/left. In this case, the two step groove portions are formed on each pulley in the axial direction thereof, the step number of grooves becomes four in total. Accordingly, as described before, each pulley has enough space for providing two step groove portions each. Therefore, the space saving in the axial direction of the pulley is again improved as in the case of the constitution presented by the first embodiment, as compared with the prior art case.

Second Embodiment

Figure 9:
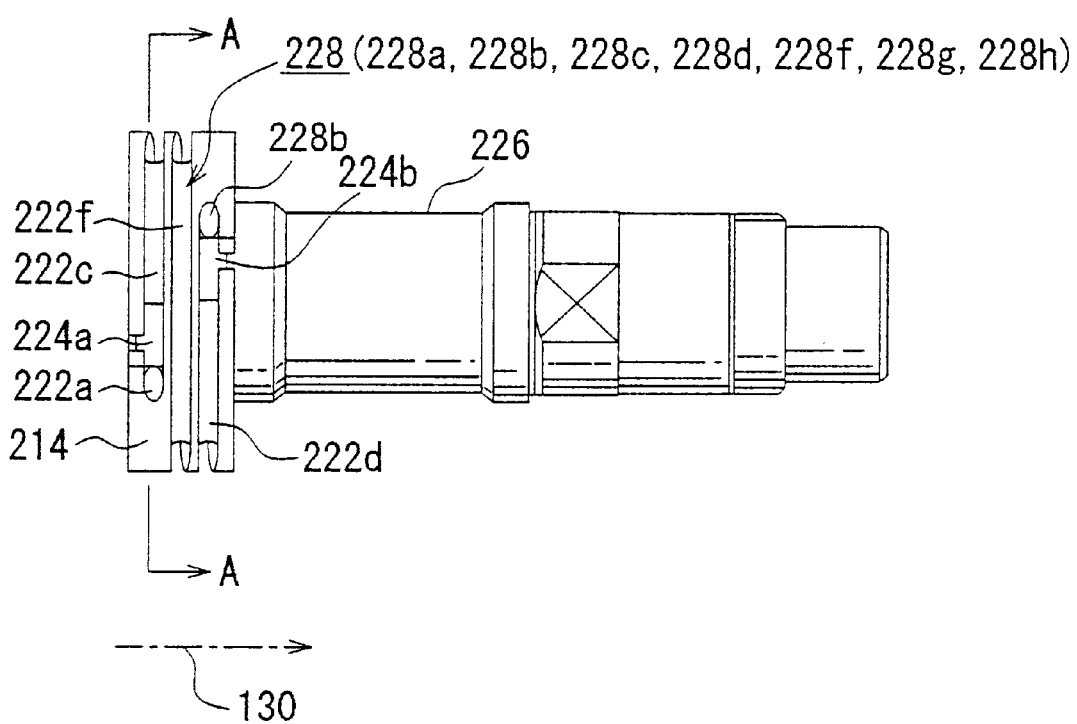
FIG. 9 is an external view showing the constitution of a pulley of the endoscope according to the second embodiment of the invention.

In the next, a pulley 214 according to the second embodiment of the invention will be described in detail with reference to FIGS. 9 through 14. FIG. 9 is a diagram showing the outside appearance of the pulley 214, FIG. 10 is a sectional side view of the pulley 214, FIG. 11 is a sectional view of the pulley 214, taken along the A–A line of FIG. 9, and FIG. 12 is an expanded plan view of the groove 228 of the pulley 214, which is obtained by cutting the pulley of the endoscope from the P position in the state shown in FIG. 11 and expanding the circumferential surface.

Figure 10:
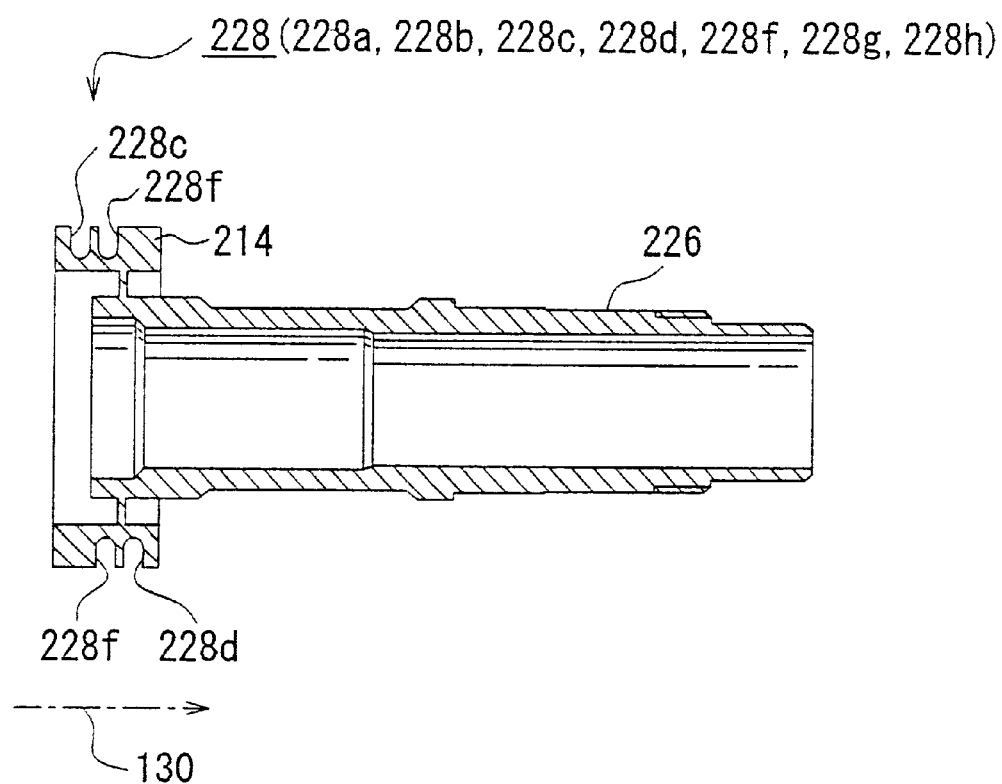
FIG. 10 is a sectional side view showing the constitution of a pulley of the endoscope according to the second embodiment of the invention.

As will be seen from FIGS. 2 and 10, the above pulley 214 is fitted to one end portion of the pulley axle 226. This pulley axle 226 is formed in the shape of an almost circular tube and the other end portion thereof is fitted to the angle knob 112 as shown in FIG. 1. To put it more concretely, the angle knob 112 has a fitting hole (not shown) as formed on its inside peripheral surface, and the pulley axle 226 is fitted to the angle knob 112 through this fitting hole. With this, the rotation of the angle knob 112 is transmitted to the pulley axle 226 to rotate it, whereby the pulley 214 is rotated by an angle corresponding to the turning angle of the angle knob 112.

Figure 11:
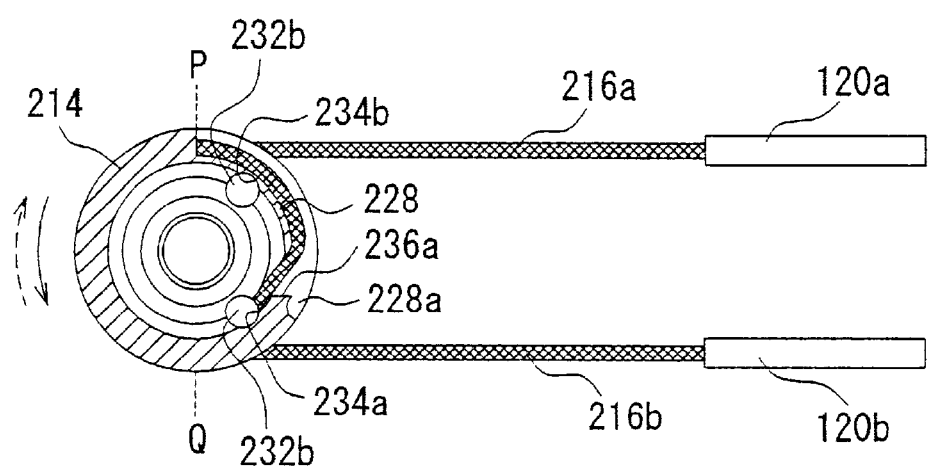
FIG. 11 is a sectional view taken along the A—A line of FIG. 9 for showing the constitution of a pulley of the endoscope according to the second embodiment of the invention.

Referring to FIG. 11, the above pulley 214 has a groove 228 as formed on the external periphery thereof, and manipulating wires 216a, 216b are taken up on the groove 228. The manipulating wires 216a, 216b are parts of control wire as same as the former embodiment. As will be seen from FIGS. 9 through 12, this groove 228 is formed in the shape of a spiral continuously extending in the peripheral direction of the above pulley 214. The groove 228 is made up of a groove portion (the first step groove portion) 228c beginning from one end 228a of the groove 228, another groove portion (the second step groove portion) 228d beginning from the other end 228b of the groove 228, and still another groove portion (middle step groove portion) 228f located in the middle between the first and second step groove portions 228c and 228d. These first, second and middle step groove portions 228c, 228d and 228f are arranged to be in parallel with one another in the axial direction of the pulley 214 as indicated by an arrow 130 (single dot chain line). The groove 228 is further provided with a shift step groove portion connecting adjacent groove portions with each other. In the example as shown, the shift step groove portion is made up of one groove portion (first transition step groove portion) 228g connecting the first step groove portion 228c with the middle step groove portion 228f and the other groove portion (second transition step groove portion) 228h connecting the middle step groove portion 228f with the second step groove portion 228d.

Figure 12:
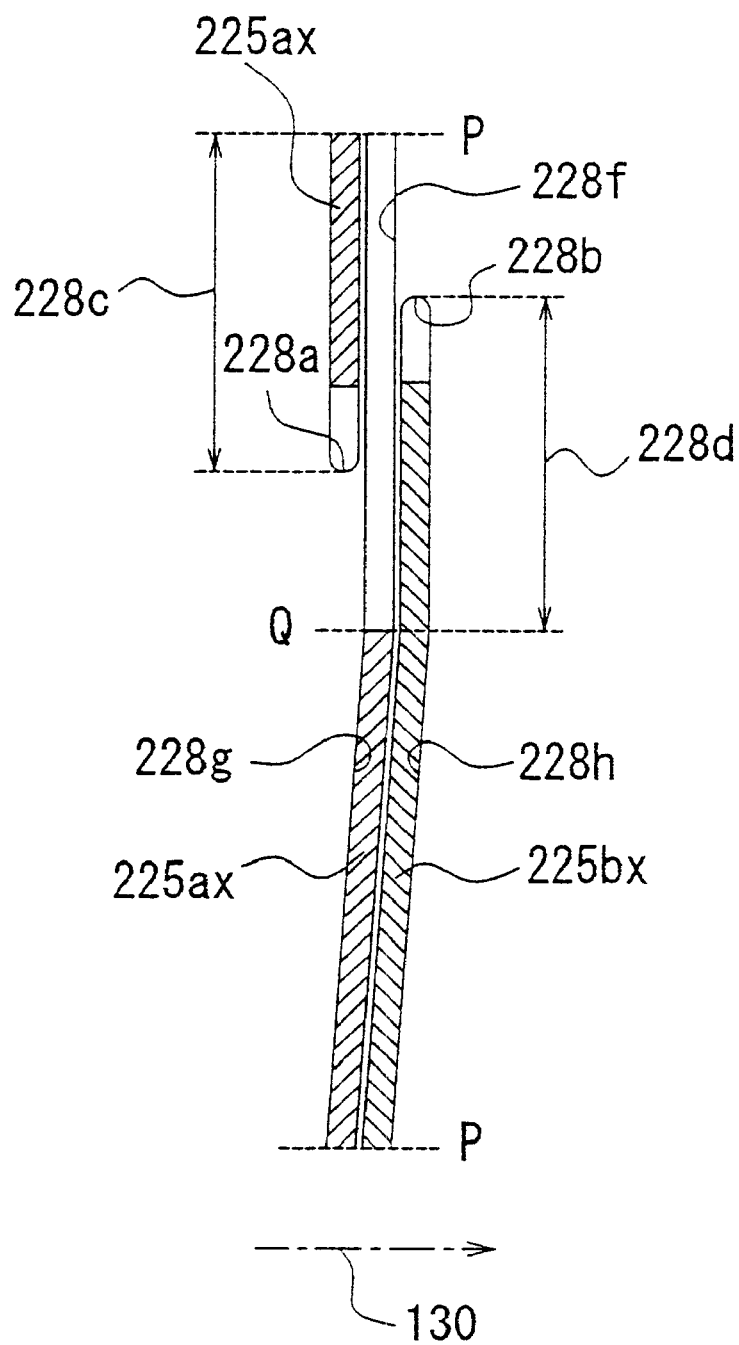
FIG. 12 is an expanded plan view of the groove of the pulley, which is obtained when cutting the pulley of the endoscope according to the second embodiment from the P position shown in FIG. 11 and expanding the circumference surface thereof.
Figure 13:
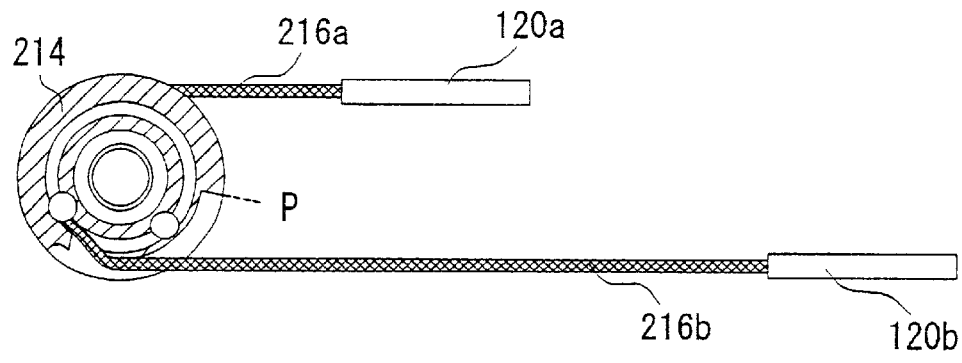
FIGS. 13(a) through 13(c) are illustrations for describing the operation of the pulley of the endoscope according to the second embodiment of the invention.
Figure 13:
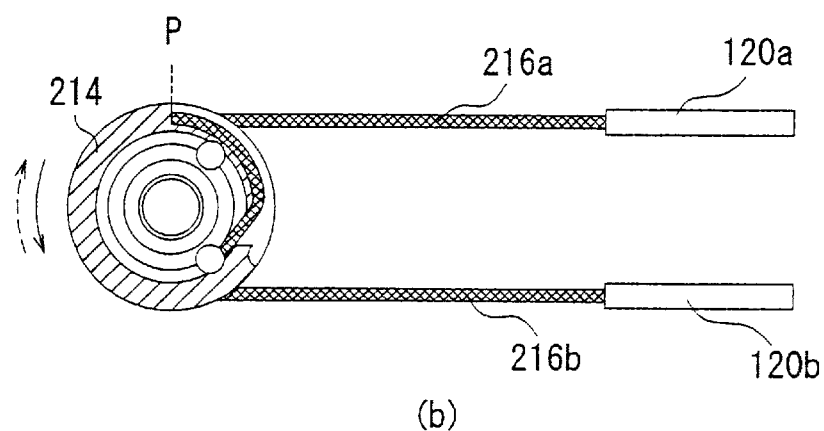
Figure 13:
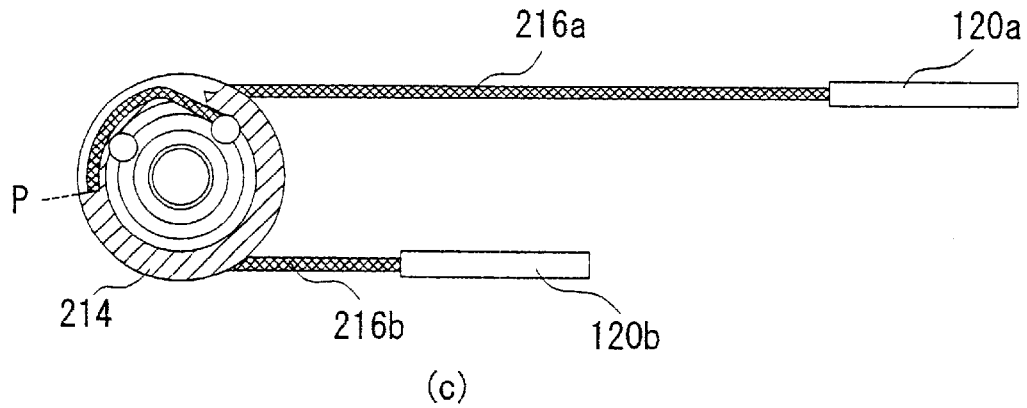
Figure 14:
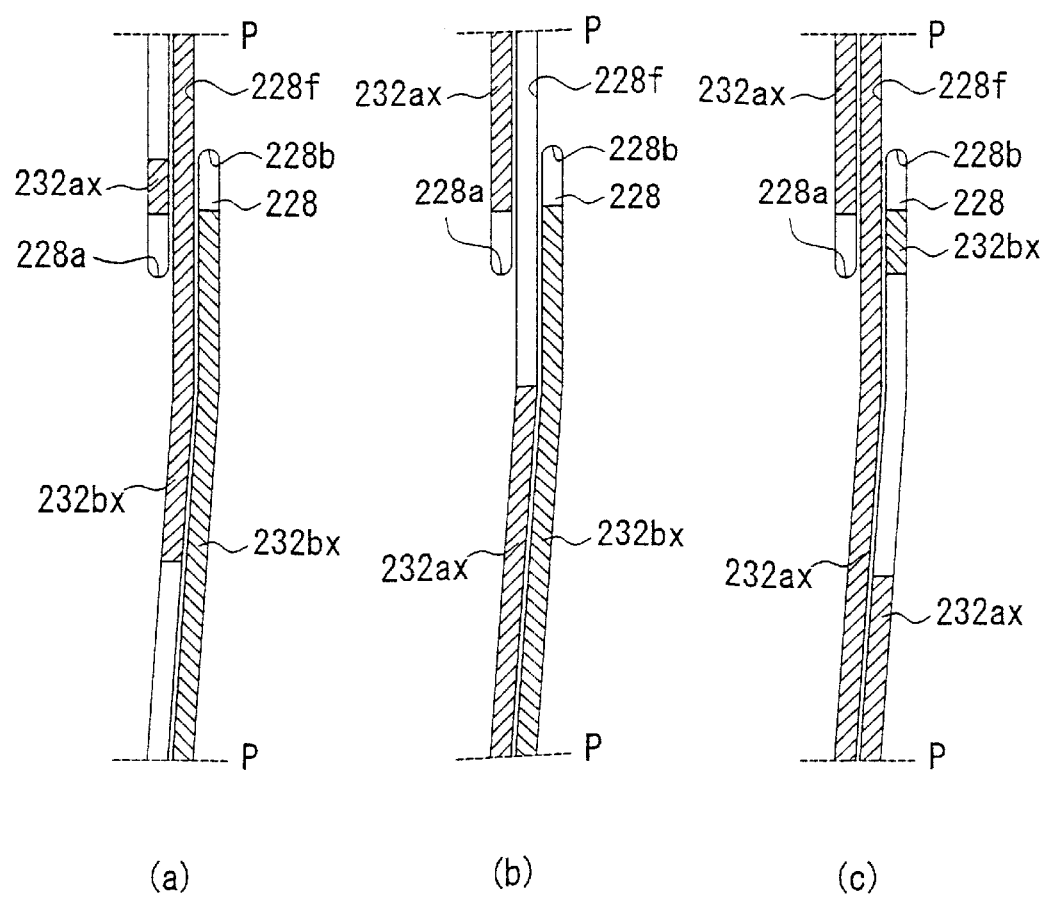
FIGS. 14(a) through 14(c) are illustrations for describing the operation of the pulley of the endoscope according to the second embodiment of the invention.
Figure 15:
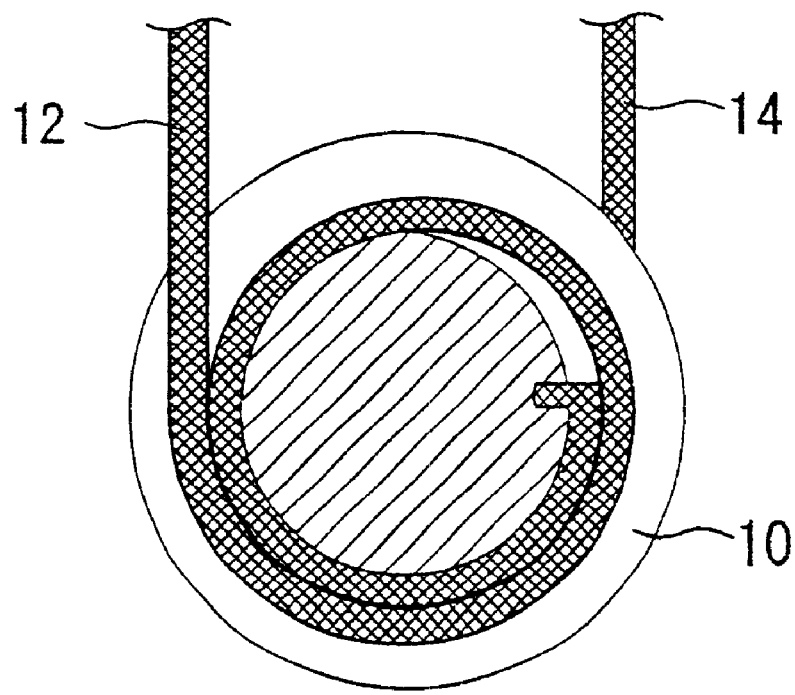
FIG. 15 is a sectional side view of the pulley provided in the bending manipulation device as has been used by the prior art endoscope.

To put it more in detail, as shown in FIG. 12, the first step groove portion 228c is formed on the first plane obtained by cutting the pulley 214 in the direction perpendicular to the axis thereof. The middle step groove portion 228f is formed on the middle plane such that it becomes in parallel with the above first step groove portion 228c, the middle plane being a plane obtained by almost parallelly shifting the first plane in the axial direction 130 of the pulley 214.

Furthermore, the second step groove portion 228d is formed on the second plane obtained by further shifting the middle plane in the axial direction 130 of the pulley 214.

That is, the first step groove portion 228c, the middle step groove portion 228f and the second step groove portion 228d are linearly expanded in the peripheral direction. The first transition step groove portion 228g is formed such that it is gradually shifted from the first plane to the second plane in the axial direction 130 of the pulley 214. Similarly, the second transition step groove portion 228h is formed such that it is gradually shifted from the second plane to the third plane in the axial direction 130 of the pulley 214. That is, the first transition step groove portion 228g and the second step groove portion 228h are expanded as slant lines respectively slanting in the axial direction 130 of the pulley 214.

As shown in FIG. 11, in the vicinity of one end 228a of the groove 228 formed on the above pulley 214, there are formed circular tube-like coupling holes 234a, 234b capable of receiving spherical coupling members 232a, 232b from the side of the pulley 214, respectively. These spherical coupling members 232a, 232b are fitted to each one end of manipulating wires 216a, 216b, respectively. To put it more concretely, as shown in FIGS. 11, for instance, the coupling hole 234a is provided in a region beyond one end 228a of the groove 228 in the peripheral direction of the pulley 214 as indicated by an arrow (solid line). On the other hand, the coupling hole 234b is provided in a region beyond the other end 228b of the groove 228 in the peripheral direction of the pulley 214 as indicated by an arrow (dotted line). Each center of coupling holes 234a, 234b is positioned so as to externally go away from the pulley axle 226 in the radius direction of the pulley 214 and positioned on the center side of the groove 228 of the pulley 214 rather than the bottom of the same.

Furthermore, as shown in FIGS. 11 and 12, in a part of one end 228a of the groove 228, there is provided a communication hole 236a communicating with the above coupling hole 234a while in a part of the other end 228b of the groove 228, there is provided another communication hole 236b communicating with the above coupling hole 234b. Still further, the above communication hole 236a opens to one side surface (left side surface as shown) of the pulley 214 as shown in FIG. 9, while the above communication hole 236b opens to the other side surface (right side surface as shown) of the pulley 214 as shown in FIG. 9.

As shown in FIG. 11, the above manipulating wire 216a inserts its coupling member 232a into the coupling hole 234a of the pulley 214 from one side surface thereof and at the same time, passes itself through the communication hole 236a, and then winds itself onto the groove 228 of the pulley 214 to set itself thereon. With this, the above manipulating wire 216a is held in the groove 228 of the pulley 214 to be workable in the take-up direction as well as in the pay-out direction. In this way, the manipulating wire 216a is taken up on the groove 228 as the pulley 214 is rotated in the direction as indicated by a solid line arrow (one direction) while it is paid out from the groove 228 as the pulley 214 is rotated in the direction as indicated by a dotted line arrow (reverse direction). The manipulating wire 216a in the state shown in FIG. 11 exists in the hatched portion 232ax as shown in FIG. 12.

Furthermore, the above manipulating wire 216b inserts the coupling member 232b into the coupling hole 234b of the pulley 214 from the other side surface thereof and at the same time, passes itself through the communication hole 136b, and then winds itself onto the groove 228 of the pulley 214 to set it thereon. With this, the above manipulating wire 216b is held in the groove 228 of the pulley 214 to be workable in the take-up direction as well as in the pay-out direction. In this way, the manipulating wire 216b is taken up on the groove 228 as the pulley 214 is rotated in the direction indicated by the dotted line arrow (reverse direction) while it is paid out from the groove 228 as the pulley 214 is rotated in the direction as indicated by the solid line arrow (one direction). The manipulating wire 216a in the state shown in FIG. 11 exists in the hatched portion 232bx as shown in FIG. 12.

In the bending manipulation device as constituted like the above according to the second preferred embodiment, the pulley 214 can be rotated in either one of two directions by means of the angle knob 112, thereby one manipulating wire 216a (or 216b) is taken up by the pulley 214 while the other manipulating wire 216b (or 216a) is paid out from the pulley 214. With this, the bending portion 108 as shown in FIG. 1 is curved at a desired angle.

The operation at this time will be described in the following, with reference to FIGS. 13(a)–13(c) and 14(a)–14(c). FIGS. 13(a) through 13(c) show the relation between the turning direction of the pulley 214 and the states of manipulating wires 216a, 216b taken up by and paid out from the pulley 214. FIGS. 14(a) through 14(c) are expanded views of the groove 228 of the pulley 214 obtained by cutting the pulley 214 from the P position in the respective turning states of the pulley 214 and then expanding only the groove 128 when manipulating wires 216a, 216b are in respective positions as shown in FIGS. 13(a) through 13(c). In the state shown in FIG. 13(b), both of manipulating wires 216a, 216b are extended out the same length from the pulley 214, so that the bending portion 108 is in the state where it is not yet curved at any angle.

If the angle knob 112 is operated at first in the state shown in FIG. 13(b) and the pulley 214 is rotated in the direction as indicated by an arrow (dotted line), the other manipulating wire 216b is taken up by the pulley 214 as shown FIG. 13(c) and at the same time, one manipulating wire 116a is paid out from the pulley 214. With this, the bending portion 108 is curved in the upward (or downward) direction, for instance.

At this time, the groove 228 of the pulley 214 is moved from the state of FIG. 14(b) to the state of FIG. 14(c). In other words, as the other manipulating wire 216b is taken up, the length of the groove 228 of the pulley 214 used by this other manipulating wire 216b gradually becomes longer, and in the state of FIG. 13(c), the manipulating wire 216b makes use of the hatched portion 232bx as shown in FIG. 14(c). In contrast, the one manipulating wire 216a is gradually paid out, so that the part of the groove 228 of the pulley 214 used by this one manipulating wire 216a gradually becomes smaller, and in the state of FIG. 13(c), the portion of the groove 228 the manipulating wire 216a makes use of is the hatched portion 232ax as shown in FIG. 14(c). In this case, it is understood that the manipulating wire 216a uses all of the middle step groove portion 228f located in the middle of the groove 228.

In the next, if the angle knob 112 is operated in the state shown in FIG. 13(b) and the pulley 214 is rotated in the direction as indicated by an arrow (solid line), one manipulating wire 216a is taken up by the pulley 214 as shown FIG. 13(a), and at the same time, the other manipulating wire 216b is paid out from the pulley 214. With this, the bending portion 108 is curved in the downward (or upward) direction, for instance.

At this time, the groove 228 of the pulley 214 is moved from the state of FIG. 14(b) to the state of FIG. 14(a). In other words, as one manipulating wire 216a is taken up by the pulley 214, the length of the groove 228 of the pulley 214 as used by this one manipulating wire 216a gradually becomes longer, and in the state of FIG. 13(a), the manipulating wire 216a makes use of the hatched portion 232ax as shown in FIG. 14(a). In contrast, the other manipulating wire 216b is gradually paid out, so that the part of the groove 228 of the pulley 214 used by this other manipulating wire 216b gradually becomes smaller, and in the state of FIG. 13(a), the portion of the groove 228 the manipulating wire 216b makes use of is the hatched portion 232bx as shown in FIG. 14(a). In this case, it is understood that the manipulating wire 216a uses all of the middle step groove portion 228f located in the middle part of the groove 228.

As described above, according to the second embodiment, the groove of the pulley 214 for taking up a pair of manipulating wires 216a, 216b thereon is made up of a single groove continuously extending in the peripheral direction of the pulley 214, so that there is no need for each of manipulating wires 216a, 216b to be doubly wound in order to earn or to increase the wire stroke. This makes it possible to prevent the rotational torque from being increased at the time of executing the bending manipulation with regard to the bending portion 108 and also to avoid self-interference by the same manipulating wire. With this, there can be provided a bending manipulation device capable of being handled with ease and enhancing the durability of the manipulating wire.

Furthermore, each of manipulating wires 216a, 216b is alternately taken up on the groove 228 of the pulley 214. In other words, as the one of manipulating wires is taken up, it gradually uses more of the groove 228 of the pulley 214, and the other of manipulating wire is gradually paid out from the groove 228 of the pulley 214, thus the groove 228 of the pulley 214 gradually coming into the unused state. Therefore, there is neither the chance that the groove 228 of the pulley 214 is used by both of manipulating wires 216a, 216b at one time, nor the chance that they interfere with each other.

Still further, as the groove of the pulley is formed in the shape of a spiral continuously extending in the peripheral direction of the pulley, each manipulating wire is extended being shifted from the pulley, so that there can be surely avoided interference between a pair of manipulating wires, the interference being caused when paying out the manipulating wire from the groove of the pulley.

Still further, as the groove 228 of the pulley 214 is formed as a single groove 228 continuously extending in the peripheral direction of the pulley, each of manipulating wires 216a, 216b can use this groove 228 in common. Consequently, the length of the groove 228 can be shortened comparing with the prior art case wherein the groove is separately prepared for every manipulating wire. Especially, in case of the second embodiment, the groove 228 of the pulley 214 is formed such that the first step groove portion 228c beginning from the one end 228a of the groove 228, the second step groove portion 228d beginning from the other end 228b of the groove 229, and a middle step groove portion 228f between the above first and second step groove portions 228c, 228d are arranged in parallel with each other in the axial direction 130 of the pulley 214. With this groove structure, there can be obtained in the axial direction 130 of the pulley 214 a good enough width or space allowing three step groove portions to be provide. Accordingly, it becomes possible to save more space in the axial direction of the pulley, as compared with the prior art case wherein space is required for four step groove portions, and to facilitate the miniaturization of the device.

Still further, according to the second embodiment, each of manipulating wires 216a, 216b is alternately taken up on the groove 228 of the pulley 214 corresponding to the turning direction of the pulley 214, so that the groove 228 of the pulley 214 can be commonly used by each of manipulating wires 216a, 216b. With this, the wire stroke of respective manipulating wires 216a, 216b can be made longer by a length obtained by the common use effect of the groove 228.

Especially, the groove 228 of the pulley 214 is made up of the first step groove portion 228c beginning from the one end 228a of the groove 228, the second step groove portion 228d beginning from the other end 228b of the groove 228, and a middle step groove portion 228f formed between the above first and second step groove portions 228c, 228d, so that each of the manipulating wire 216a, 216b can be taken up on the groove 228 with a larger amount. Therefore, wire stroke of respective manipulating wires 216a, 216b can be made larger.

When the lengths of respective manipulating wires 216a, 216b paid out from the pulley 214 are equal to each other, it might be considered that the larger the amount of the manipulating wire taken up by the pulley 214 is, the longer manipulating wires 216a, 216b can be paid out from the pulley 214 by rotation thereof. However, according to the invention, due to existence of the middle step groove portion 228f, it becomes possible to have each of manipulating wires 216a, 216b extended out from the one side (P position) and the other side (Q position) as well of the middle step groove portion 228f as shown in FIGS. 11 and 12. Because of this, it becomes possible to increase, without interference between manipulating wires 216a, 216b, the amount of each of manipulating wires 216a and 216b taken up by the pulley 214 from its start position fixedly held on the pulley 214. Accordingly, manipulating wires 216a, 216b can be paid out longer from the pulley 214 by rotation thereof. With this, the wire stroke of the manipulating wire 216a, 216b can be made still larger.

Still further, according to the second embodiment, one manipulating wire fixedly holds its one end in the vicinity of the one end 228a of the groove 128 while the other manipulating wire fixedly holds its one end in the vicinity of the other end 228b of the groove 228. With this structure, it becomes possible to use a still longer part of the groove 228 at the time of taking up and paying out the manipulating wire and also, it becomes possible to make the wire stroke of the manipulating wire as long as possible.

The groove 228 formed on the above pulley 214 may be formed in the shape of a spiral continuously extending in the peripheral direction of the pulley 214. Accordingly, as will be known by analogy from FIG. 8, the groove 228 may be formed so as to be gradually and continuously slanted in the axial direction 130 of the pulley 214.

The second embodiment has been described so far by way of the example wherein the bending manipulation is carried out to direct the bending portion 108 in the up and down directions by means of two manipulating wires 216a, 216b. However, as a matter of course, the invention should not be limited by this example. The bending manipulation can be executed to direct the bending portion 108 in the right and left directions by means of two manipulating wires 216a, 216b.

If there are additionally provided the following items, that is, another angle knob, another pulley rotated independently by the above another angle knob and provided with the same groove as the groove 228 of the existing pulley 214 as previously described, and the same two manipulating wires fitted to another pulley as those fitted to the existing pulley 214, the bending manipulation can be carried out to direct the bending portion 108 in two kinds of directions, that is, the directions of up/down and right/left. In this case, the three groove portions are formed on each pulley in the axial direction thereof, thus the step number of groove portion becoming six in total. Accordingly, as described before, each pulley has an enough space for receive three step groove portions each. Therefore, the space saving in the axial direction of the pulley is much more improved by the constitution presented by the second embodiment, comparing with the prior art case wherein eight step groove portions are indispensably required, and miniaturization of the device is further facilitated.

In this second embodiment, the middle step groove portion 228f is formed as a single step groove portion. However, it may be made up of a plurality of middle step groove portions which are arranged almost in parallel in the axial direction of the pulley, thereby increasing the stroke of the manipulating wire.

While preferred embodiments of the invention have been shown and described with reference to the accompanying drawings, it is needless to say that the invention should not be limited by these examples. It will be apparent to those skilled in the art that various changes and modifications can be made without departing from the principle and spirit of the invention, the scope of which is defined in the appended claims, and it is understood that those changes and modifications belong to the technical scope of the invention.

What is claimed is:

1. A bending manipulation device for an endoscope having a main control portion, comprising:
    a pulley adapted for inclusion in, and to be given a rotary motion by said main control portion; and
    at least a pair of control wires, each of which winds one end portion thereof on to said pulley and extends out the other end portion thereof from said pulley such that one of the extended control wires is taken up by said pulley while the other of the same is paid out from said pulley corresponding to the rotation of said pulley, thereby enabling the bending manipulation over the bending portion to be carried out;
    said pulley having at least one common groove formed along the periphery of said pulley to continuously extend in the peripheral direction of said pulley, and wound in common by said pair of control wires, wherein said common groove is formed as a spiral groove slanting in the axial direction of said pulley.

2. A bending manipulation device for an endoscope having a main control portion, comprising:
    a pulley adapted for inclusion in, and to be given a rotary motion by said main control portion; and
    at least a pair of control wires, each of which winds one end portion thereof onto said pulley and extends out the other end portion thereof from said pulley such that one of the extended control wires is taken up by said pulley while the other of the same is paid out from said pulley corresponding to the rotation of said pulley, thereby enabling the bending manipulation over the bending portion to be carried out;
    said pulley having at least one common groove formed along the periphery of said pulley to continuously extend in the peripheral direction of said pulley, and wound in common by said pair of control wires, wherein said common groove is formed in multiple steps.

3. A bending manipulation device for an endoscope as claimed in claim 2, wherein said common groove is made up of a first step groove portion expanded on a first plane beginning from one end of said common groove and perpendicular to the axis of said pulley, a middle step groove portion expanded on a second plane beginning from the other end of said common groove, obtained by shifting said first plane in the axial direction of said pulley, and a shift step groove portion providing communication between said first step groove portion and said middle step groove portion.

4. A bending manipulation device for an endoscope as claimed in claim 2, wherein said common groove is made up of
    a plurality of successively adjacent step groove portions, including a first step groove portion expanded on a first plane beginning from one end of said common groove and perpendicular to the axis of said pulley, a middle step groove portion expanded on a second plane beginning from the other end of said common groove, obtained by shifting said first plane in the axial direction of said pulley, at least one middle step groove portion expanded on a middle plane located in the middle between said first and second planes to be in parallel therewith, and
    a shift step groove portion providing communication between said adjacent step groove portions.

5. A bending manipulation device for an endoscope comprising:
    a plurality of pulleys each having a respective axis of rotation;
    means supporting the pulleys for rotation about the respective axes; and
    a plurality of pairs of control wires each pair taken up by a corresponding one of said plurality of pulleys;
    said plurality of pulleys having a plurality of common grooves, each being formed in a respective one said pulleys such that each pair of control wires corresponds to one common groove on the one pulley taking up the pair of control wires, wherein each common groove is formed as a spiral groove slanting in the axial direction of said pulley.

6. A bending manipulation device for an endoscope comprising:
    a plurality of pulleys each having a respective axis of rotation;
    means supporting the pulleys for rotation about the respective axes; and
    a plurality of pairs of control wires each pair taken up by a corresponding one of said plurality of pulleys;
    said plurality of pulleys having a plurality of common grooves, each being formed in a respective one of said pulleys such that each pair of control wires corresponds to one common groove on the one pulley taking up the pair of control wires, wherein said common groove is formed in multiple steps.

7. A bending manipulation device for an endoscope as claimed in claim 6, wherein each of said plurality of common grooves is made up of a first step groove portion expanded on a first plane beginning from one end of said common groove and perpendicular to the axis of the pulley on which the common groove is formed, a middle step groove portion expanded on a second plane beginning from the other end of said common groove, obtained by shifting said first plane in the axial direction of said pulley, and a shift step groove portion providing communication between said first step groove portion and said middle step groove portion.

8. A bending manipulation device for an endoscope as claimed in claim 6, wherein each of said plurality of common grooves is made up of a plurality of successively adjacent step groove portions, including a first step groove portion expanded on a first plane beginning from one end of said common groove and perpendicular to the axis of the pulley on which the common groove is formed, a middle step groove portion expanded on a second plane beginning from the other end of said common groove, obtained by shifting said first plane in the axial direction of said pulley, at least one middle step groove portion expanded on a middle plane located in the middle between said first and second planes to be in parallel therewith, and a shift step groove portion providing communication between said adjacent step groove portions.

* * * * *